US009588055B2

(12) United States Patent
Urano et al.

(10) Patent No.: US 9,588,055 B2
(45) Date of Patent: Mar. 7, 2017

(54) DEFECT INSPECTION APPARATUS AND DEFECT INSPECTION METHOD

(71) Applicant: Hitachi High-Technologies Corporation, Minato-ku, Tokyo (JP)

(72) Inventors: Yuta Urano, Tokyo (JP); Taketo Ueno, Tokyo (JP); Akira Hamamatsu, Tokyo (JP); Toshifumi Honda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/331,681

(22) Filed: Jul. 15, 2014

(65) Prior Publication Data
US 2015/0062581 A1    Mar. 5, 2015

(30) Foreign Application Priority Data
Aug. 30, 2013  (JP) .................................. 2013-178806

(51) Int. Cl.
*G01N 21/00*  (2006.01)
*G01N 21/88*  (2006.01)
(Continued)

(52) U.S. Cl.
CPC ......... *G01N 21/8806* (2013.01); *G01N 21/21* (2013.01); *G01N 21/9501* (2013.01);
(Continued)

(58) Field of Classification Search
CPC ... G01N 2021/8845; G01N 2021/8848; G01N 21/21; G01N 21/8806; G01N 21/9501; G01N 21/956
See application file for complete search history.

(56) References Cited

U.S. PATENT DOCUMENTS 4,919,534 A * 4/1990 Reed ..................... B07C 5/3416
   209/524
4,952,058 A * 8/1990 Noguchi et al. .......... 356/237.5
(Continued)

FOREIGN PATENT DOCUMENTS

JP          2012-068261 A       4/2012

*Primary Examiner* — Kara E Geisel
*Assistant Examiner* — Rufus Phillips
(74) *Attorney, Agent, or Firm* — Miles & Stockbridge P.C.

(57) ABSTRACT

A defect inspection apparatus includes: a seed light generator including a pulse signal generator that generates a pulse signal and a polarization modulator that outputs pulse light of any one of two polarization states orthogonal to each other in synchronization with the pulse signal output from the pulse signal generator; a wavelength converting unit including a branching mechanism that branches the pulse light output by the polarization modulator of the seed light generator using polarization and a converting unit that wavelength-converts the pulse light branched by the branching mechanism into beams of two different wavelengths, respectively; an illumination optical system that illuminates a surface of an inspected target material with the beams of the two different wavelengths converted by the wavelength converting unit; a detection optical system including a detecting unit that detects light generated by the beams of the two different wavelengths illuminated by the illumination optical system; and a signal processing system including a distributor that distributes a signal based on the light detected by the detecting unit of the detection optical system for each wavelength, on the basis of the pulse signal output from the pulse signal generator, and a defect determining unit that processes a signal based on the light distributed by the distributor and determines a defect.

8 Claims, 10 Drawing Sheets

(51) Int. Cl.
*G01N 21/21* (2006.01)
*G01N 21/95* (2006.01)
*G01N 21/956* (2006.01)

(52) U.S. Cl.
CPC ... *G01N 21/956* (2013.01); *G01N 2021/8845* (2013.01); *G01N 2021/8848* (2013.01)

(56) References Cited

U.S. PATENT DOCUMENTS

| | | | | |
|---|---|---|---|---|
| 5,357,960 | A * | 10/1994 | Schmidtke | A61B 5/14558 356/364 |
| 5,486,919 | A * | 1/1996 | Tsuji | G01N 21/88 356/237.4 |
| 6,822,978 | B2 * | 11/2004 | Kafka et al. | 372/18 |
| 7,339,661 | B2 * | 3/2008 | Korngut et al. | 356/237.2 |
| 2008/0297783 | A1 | 12/2008 | Urano et al. | |
| 2013/0235374 | A1 * | 9/2013 | Biellak et al. | 356/237.5 |

* cited by examiner

DEFECT INSPECTION APPARATUS AND DEFECT INSPECTION METHOD

CROSS-REFERENCE TO RELATED APPLICATIONS

This application claims the priority of Japanese Patent Application No. 2013-178806, filed on Aug. 30, 2013, which is incorporated herein by reference in its entirety.

BACKGROUND OF THE INVENTION

1. Field of the Invention

The present invention relates to a defect inspection apparatus and a defect inspection method that inspect an occurrence situation of a defect to detect the defect occurring in a manufacturing process such as a semiconductor manufacturing process, a liquid crystal display element manufacturing process, and a printed circuit board manufacturing process for forming a pattern on a substrate and making an target material, analyze the defect, and take measures.

2. Description of the Related Art

As the related art of a field of the present technology, there is JP-2012-68261-A. In JP-2012-68261-A, "a defect inspection method that includes illuminating for guiding light emitted from a light source to a predetermined region on an inspection target substrate under a plurality of predetermined optical conditions, detecting for guiding a scattered light component propagated to a predetermined azimuth angle range and a predetermined elevation angle range to an optical receiver for each of a plurality of scattered light distributions generated in correspondence with the plurality of optical conditions in the predetermined region and obtaining electrical signals, and determining a defect on the basis of a plurality of electrical signals obtained in the detection" is described.

SUMMARY OF THE INVENTION

By a defect and a material constant of an inspection target substrate surface, particularly, wavelength dependency of an optical refraction index and a relative relation of a thickness of a film formed on the inspection target substrate surface and a wavelength, a defect signal may not be obtained or noise may increase and a defect may not be detected for a certain wavelength in specific defect material, defect dimension, defect shape, film material quality, and film thickness. Therefore, in a defect inspection apparatus that uses only light of a predetermined single wavelength for an inspection, sufficient defect detection sensitivity may not be obtained depending on an inspection target.

In JP-2012-68261-A described above, the defect inspection apparatus using the light of the plurality of wavelengths is described. However, in the defect inspection apparatus using the plurality of wavelengths described in JP-2012-68261-A, because a light source, a detector, and a signal processing system corresponding to each of the used wavelengths are necessary, the scale of the apparatus increases and a cost thereof increases. Meanwhile, if one optical system is used to change the wavelength for each inspection sequence every time and perform the inspection, the inspection of the plurality of wavelengths can be performed by a cheap apparatus. However, the inspection cannot be completed in short time.

If "emitting the light of the plurality of wavelengths by the single light source" described in JP-2012-68261-A is used, the number of necessary light sources can be decreased. However, a specific configuration of such light source is not described. In addition, a configuration example of "changing illumination conditions and detection conditions over time" is described. However, changing the wavelength over time as optical conditions is not described.

Accordingly, the present invention provides a defect inspection apparatus that can perform an inspection of a plurality of wavelengths at a high speed with a cheap configuration.

To achieve the above object, the present invention provides a defect inspection apparatus including: a seed light generator including a pulse signal generator that generates a pulse signal and a polarization modulator that outputs pulse light of any one of two polarization states orthogonal to each other in synchronization with the pulse signal output from the pulse signal generator; a wavelength converting unit including a branching mechanism that branches the pulse light output by the polarization modulator of the seed light generator using polarization and a converting unit that wavelength-converts the pulse light branched by the branching mechanism into beams of two different wavelengths, respectively; an illumination optical system that illuminates a surface of an inspected target material with the beams of the two different wavelengths converted by the wavelength converting unit; a detection optical system including a detecting unit that detects light generated by the beams of the two different wavelengths illuminated by the illumination optical system; and a signal processing system including a distributor that distributes a signal based on the light detected by the detecting unit of the detection optical system for each wavelength, on the basis of the pulse signal output from the pulse signal generator, and a defect determining unit that processes a signal based on the light distributed by the distributor and determines a defect.

According to the present invention, a defect inspection apparatus that can perform an inspection of a plurality of wavelengths at a high speed with a cheap configuration can be provided.

Other objects, configuration and effects of the invention will become apparent from the following description of embodiments.

DESCRIPTION OF THE PREFERRED EMBODIMENTS

Hereinbelow, embodiments of the present invention will be described in detail below with reference to the accompanying drawings.

First Embodiment

In this embodiment, an example of a defect inspection apparatus that can perform an inspection of a plurality of wavelengths at a high speed with a cheap configuration will be described.

Figure 1:
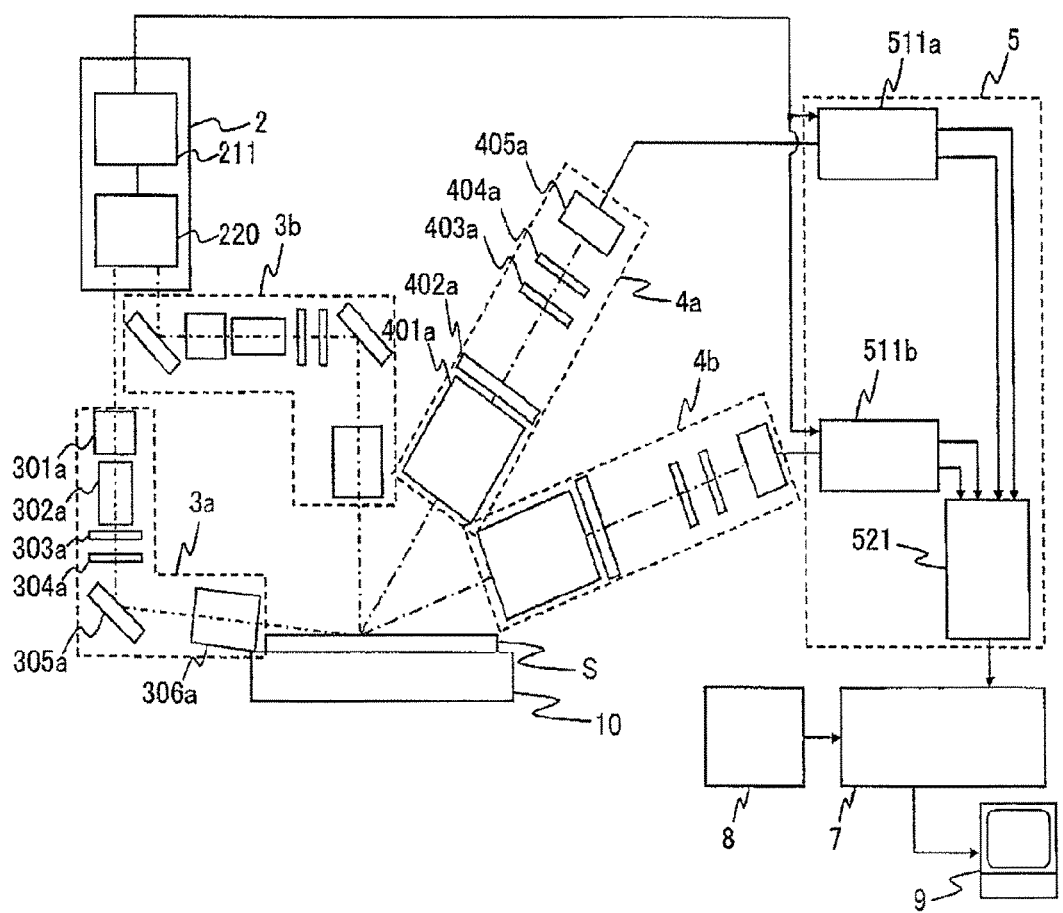
FIG. 1 is a diagram illustrating an example of a configuration of a defect inspection apparatus according to this embodiment.

FIG. 1 illustrates an example of a configuration of a defect inspection apparatus according to this embodiment. The defect inspection apparatus includes a light source 2, illumination optical systems 3a and 3b, a sample stage 10, detection optical systems 4a and 4b, a signal processing unit 5, a control unit 7, an input unit 8, and a display unit 9.

The light source 2 has a seed light generator 211 and a wavelength converting unit 220 and emits laser beams of two wavelengths. The illumination optical system 3a has an attenuator 301a, a beam expander 302a, a λ/2 plate 303a, a λ/4 plate 304a, a mirror 305a, and an illumination condensing system 306a. The illumination optical system 3b has the same configuration as the illumination optical system 3a. A laser beam of each wavelength emitted from the light source 2 passes through any one of the illumination optical system 3a and the illumination optical system 3b, is controlled in intensity, polarization state, beam diameter, and incidence angle thereof, is condensed on a sample S arranged on a sample stage 10, and is radiated. The illumination optical system 3a radiates illumination light to the sample S in an oblique direction. The illumination optical system 3b radiates the illumination light to the sample S in a vertical direction.

It is effective to guide the laser beam of the short wavelength of the two wavelengths of the laser beams emitted from the light source 2 to the illumination optical system 3a and guide the laser beam of the long wavelength to the illumination optical system 3b, because both short wavelength oblique illumination effective for detection a minute foreign material or a convex defect and long wavelength vertical illumination effective for detection of a low level difference defect or a concave defect can be realized. Because it may be effective to reverse a wavelength and an illumination incidence angle depending on a target sample or a defect, in this case, a position of a mirror between the light source and the illumination optical systems 3a and 3b is changed, so that the short wavelength oblique illumination and the long wavelength vertical illumination are realized. When the wavelengths of the laser beams input to the illumination optical systems 3a and 3b are changed, position adjustment of an optical axis direction of a beam expander constituent element, exchanging of the wavelength plate to the wavelength plate of the corresponding wavelength, and focus adjustment of the illumination condensing systems 306a and 306b are performed according to necessity. According to the configuration described above, because the number of the wavelengths of the laser beams incident on the illumination optical systems 3a and 3b at a time is one, the wavelength plates corresponding to the plurality of wavelengths, the beam expander in which chromatic aberration has been corrected, and the illumination condensing systems become unnecessary. As a result, the illumination optical systems can be mounted at a low cost.

Scattered light from a region (illumination spot) on the sample S on which the light has been radiated by the illumination optical systems 3a and 3b is detected by the detection optical systems 4a and 4b. The detection optical system 4a has a detection condensing system 401a, a space filter 402a, a λ/4 plate 403a, a polarization plate 404a, and an optical detector 405a. Scattered light of a plurality of wavelengths corresponding to the plurality of wavelengths of the light emitted from the light source 2 is generated from the illumination spot. The generated scattered light is condensed by the detection condensing system 401a, a scattered light component of a scattered direction or a polarization state having large noise is shielded or reduced by the space filter 402a, the λ/4 plate 403a, and the polarization plate 404a, and the scattered light is detected by the optical detector 405a.

The detection condensing system 401a is configured using a refraction optical system including lenses of a plurality of materials, a catadioptric system including a curved reflection surface in which there is not the chromatic aberration, or a reflection optical system to suppress the wavelength dependency and the chromatic aberration. The optical detector 405a has a sensitivity wavelength region in which the plurality of wavelengths of the light emitted from the light source 2 can be detected. In addition, the optical detector 405a is a detector of a high-speed response that has a response speed shorter than a pulse interval of a repetitive pulse signal generated by a pulse signal generator 101 to be described below. The detection optical system 4b has the same configuration as the detection optical system 4a and detects scattered light emitted in a direction different from a light emission direction of the detection optical system 4a.

The signal processing unit 5 has distributors 511a and 511b and a defect determiner 521. Signals of scattered light of a plurality of wavelengths detected by the optical detectors 405a and 405b are separated by the distributors 511a and 511b for each wavelength, the presence or absence of a defect is determined by the defect determiner 521 on the basis of the signals, and a determination result is output.

The control unit 7 controls the individual units of the defect inspection apparatus, on the basis of an input from the input unit 8. In addition, a scattered light detection signal output from the signal processing unit 5 and information of the defect are stored in a storage medium of the control unit 7 and are output to the display unit 9 according to an instruction from the input unit or a setting value.

Figure 2:
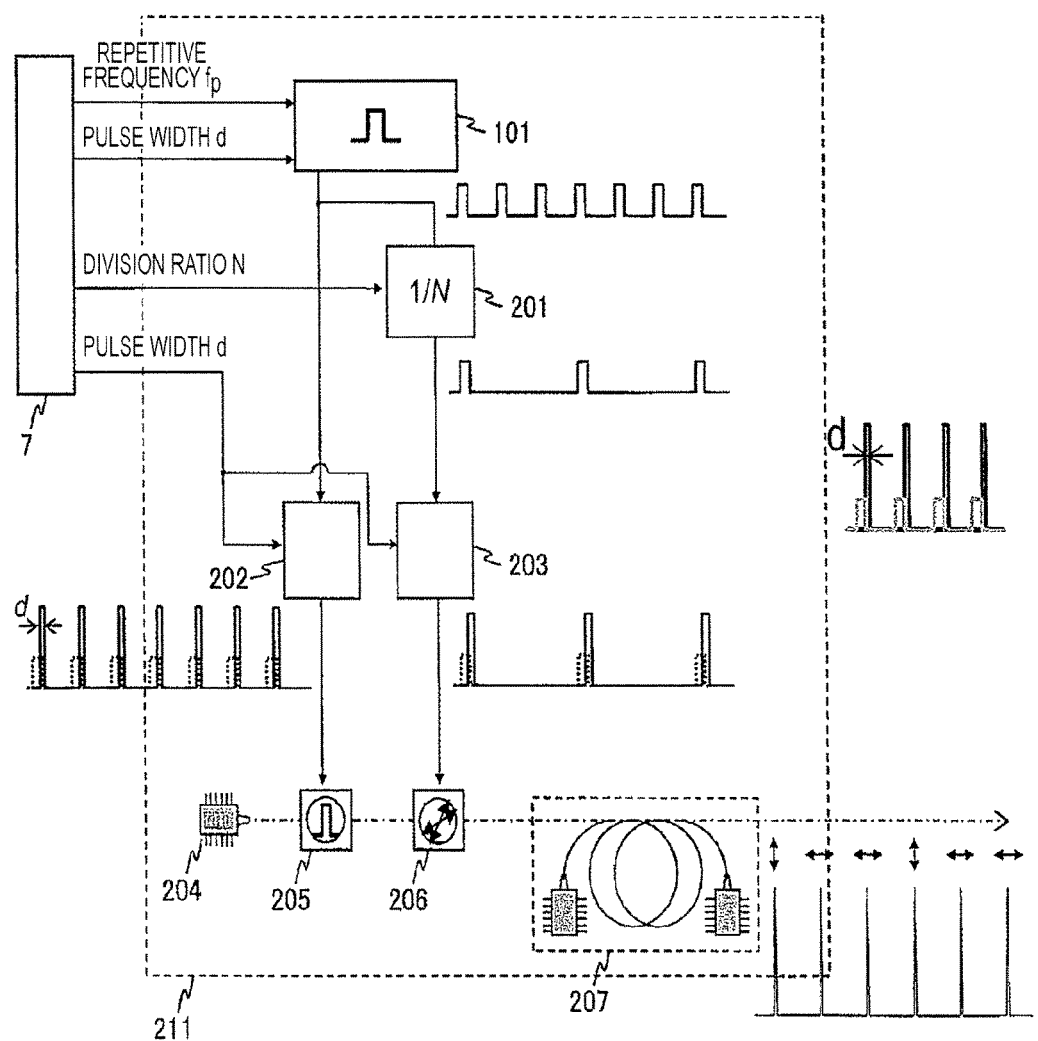
FIG. 2 is a diagram illustrating an example of a configuration of a seed light generator according to this embodiment.

FIG. 2 illustrates an example of a configuration of the seed light generator 211 according to this embodiment. The light source 2 has a pulse signal generator 101, a division signal generator 201, an intensity modulator driver 202, a polarization modulator driver 203, a laser diode 204, a light intensity modulator 205, a polarization modulator 206, and an optical amplifier 207.

The pulse signal generator 101 generates a repetitive pulse signal and the intensity modulator driver 202 drives the intensity modulator 205 on the basis of the repetitive pulse signal. The repetitive pulse signal is input to the division signal generator 201, a division signal is input to the polarization modulator driver, and the polarization modulator driver 203 drives the polarization modulator 206 on the basis of the division signal. A repetitive frequency and a pulse width of an output of the pulse signal generator 101, a division ratio of an output of the division signal generator 201, a pulse width of an output of the intensity modulator driver 202, and a pulse width of an output of the polarization modulator driver 203 are set and adjusted by the control unit 7.

The laser diode 204 is a distributed feedback (DFB) laser of a wavelength range of 1064 nm and outputs a high-output laser beam of a stabilized wavelength at a small spectral width in a single mode. The laser beam is pulse-modulated by the light intensity modulator 205 and is polarization-modulated by the polarization modulator 206. When a division ratio of the division signal generator 201 is N, the polarization modulator 206 executes the following polarization modulation operation. The polarization modulator 206 polarization-modulates a polarization state of a first pulse to a polarization state orthogonal to an original polarization state. The polarization modulator 206 passes a laser beam of the original polarization state, without changing a polarization state of second and following pulses, for example, a polarization state of an N-th pulse. By the polarization modulation operation, a train of repetitive pulse light in which polarization pulse light having polarization states orthogonal to each other are arranged with a pulse number ratio of 1:(N−1) is generated. FIG. 2 illustrates an example of a train of pulse light in the case in which N is 3. Because a polarization degree is increased to raise efficiency of a pulse separation by a polarization beam splitter to be described below, a polarization plate is arranged between the laser diode 204 and the polarization modulator 206 according to necessity. As an example of a combination of the polarization states orthogonal to each other, a combination of vertical polarization and horizontal polarization or a combination of clockwise circular polarization and counterclockwise circular polarization is used. As the optical amplifier 207, an Nd doped polarization maintaining fiber that amplifies light having a wavelength of 1064 nm is used. The polarization pulse light is amplified by the optical amplifier 207 in a state in which a polarization state is maintained and is output. By the seed light generator 211 having the configuration described above, repetitive pulse light (seed light) having a wavelength of 1064 nm polarization-modulated at a high output and high peak power is obtained.

Figure 3:
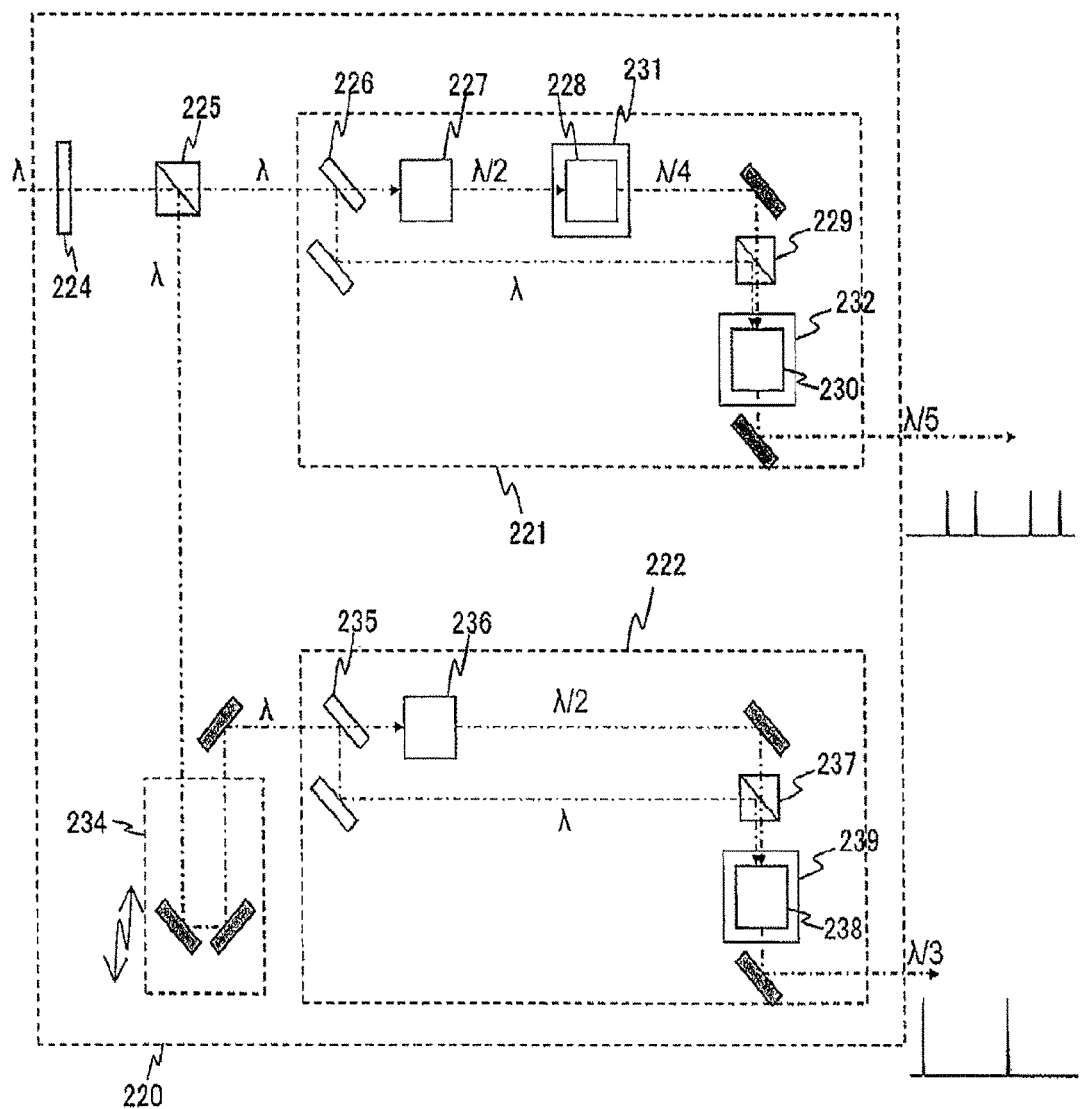
FIG. 3 is a diagram illustrating an example of a configuration of a wavelength converting unit according to this embodiment.

FIG. 3 illustrates an example of a configuration of the wavelength converting unit 220 according to this embodiment. The wavelength converting unit 220 has a wavelength plate 224, a polarization beam splitter 225, a fifth harmonic converting unit 221, a third harmonic converting unit 222, and a pulse delay unit 234. Seed light (a wavelength of 1064 nm) output by the seed light generator 211 is adjusted in polarization state by the wavelength plate 244, is branched by the polarization beam splitter 225, is converted into fifth harmonics (a wavelength of 213 nm) by the fifth harmonic converting unit 221, and is converted into third harmonics (a wavelength of 355 nm) by the third harmonic converting unit 222. The pulse delay unit 234 compensates for a difference of optical path lengths of the fifth harmonic converting unit 221 and the third harmonic converting unit 222. When a combination of the polarization states of the seed light orthogonal to each other is the clockwise circular polarization and the counterclockwise circular polarization, the seed light is converted into linearly polarized light of which polarization states are orthogonal to each other, using a λ/4 plate as the wavelength plate 224. When the seed light is the linearly polarized light of which the polarization states are orthogonal to each other, the polarization direction is adjusted to increase a separation degree of pulses by the polarization beam splitter 225, using a λ/2 plate as the wavelength plate 224 according to necessity. In the polarization beam splitter 225, the linearly polarized light of which the polarization states are orthogonal to each other are guided to different optical paths, respectively. When a division ratio of the division signal generator 201 is N, a ratio of pulse numbers per unit time in a beam incident on the fifth harmonic converting unit 221 and a beam incident on the third harmonic converting unit 222 becomes (N−1):1 and an intensity ratio becomes (N−1):1 in proportion to the ratio the pulse numbers.

One beam separated by the polarization beam splitter 225 is incident on the fifth harmonic converting unit 221. The beam is branched by a beam splitter 226, a wavelength of the beam is converted into a wavelength of 532 nm (second harmonics) by second harmonic generation by a wavelength conversion crystal 227 and is converted into a wavelength of 266 nm (fourth harmonics) by second harmonic generation by a wavelength conversion crystal 228 again, the beam is synthesized with a beam branched into a different optical path by the beam splitter 226 by a dichroic mirror 229, the wavelength of the beam is converted into a wavelength of 213 nm (fifth harmonics) by sum frequency generation by a wavelength conversion crystal 230, and the beam is output.

After an optical path difference of another beam separated by the polarization beam splitter 225 and other beam is adjusted by the pulse delay unit 234 configured using a folding mirror or a corner cube, the beam is incident on the third harmonic converting unit 222. The beam is branched by a beam splitter 235, a wavelength of the beam is converted into a wavelength of 532 nm (second harmonics) by second harmonic generation by a wavelength conversion crystal 236, the beam is synthesized with a beam branched into a different optical path by the beam splitter 235 by a dichroic mirror 237, the wavelength of the beam is converted into a wavelength of 355 nm (third harmonics) by sum frequency generation by a wavelength conversion crystal 238, and the beam is output.

By using the fifth harmonics having the short wavelength, scattered light intensity of a minute defect increases and the minute defect can be detected with high sensitivity. In addition, by using the third harmonics together, a defect in which detection is difficult due to an influence of material dependency or film thickness dependency in the fifth harmonics can be captured.

As the wavelength conversion crystals 227 and 236, an LBO crystal (LiB3O5) or a KDP crystal (KH2PO4) is used. As the wavelength conversion crystals 228 and 236, a CLBO crystal (CsLiB6O10) and a BBO crystal (β-BaB2O4) are used. As the wavelength conversion crystal 238, the LBO crystal, the BBO crystal, or a KTP crystal (KTiOPO4) is used. In the CLBO crystal and the BBO crystal, conversion efficiency is high and a damage threshold is high. However, in the CLBO crystal and the BBO crystal, because deliquescence is high, humidity needs to be managed. The crystals are placed in highly airtight temperature/humidity adjustors 231, 232, and 239 and the temperature is maintained at about 150° C. to prevent the moisture, so that a stabilized output beam is obtained. Because the deliquescence of the KDP crystal and the KTP crystal is low, a stabilized output beam can be obtained without performing such rigorous humidity management.

As described above, when wavelength conversion based on a nonlinear optical effect is performed, high peak power of pulse light is advantageous to raise efficiency of the wavelength conversion. If the polarization is not changed for each pulse in the seed light generator 211 and polarization of a beam incident on the beam splitter 225 is adjusted to branch the beam by the intensity ratio of (N−1):1, pulse peak power of the branched beam decreases to (N−1)/N and 1/N of pulse peak power of the original beam. Meanwhile, in this embodiment, because each pulse is incident on any one of the fifth harmonic converting unit 221 and the third harmonic converting unit 222, the pulse peak power is maintained before and after the branching and high wavelength conversion efficiency is obtained.

By adjusting a setting value of the division ratio N of the division signal generator 201, a light intensity ratio of the wavelength of 213 nm and the wavelength of 355 nm is adjusted. It is desirable to adjust the division ratio N such that outputs of an optical detector 405 of a rear step approach to each other between two wavelengths. As specific setting examples, there are a method of performing setting such that outputs of the fifth harmonic converting unit 221 and the third harmonic converting unit 222 become equal to each other between two wavelengths, a method of performing setting such that scattered light outputs from a minute defect become equal to each other, and a method of performing setting such that outputs of the optical detector 405a become equal to each other.

Because configurations of the wavelength conversions are different in the fifth harmonic converting unit 221 and the third harmonic converting unit 222, conversion efficiencies are different. In general, because conversion efficiency becomes low when an order of harmonics becomes high, the conversion efficiency is high in the third harmonic generation rather than the fifth harmonic generation. For example, when a conversion efficiency ratio of the fifth harmonic converting unit 221 and the third harmonic converting unit 222 is 1:10, it is desirable to set the division ratio to 11 to perform setting such that outputs of the fifth harmonic converting unit 221 and the third harmonic converting unit 222 become equal to each other between the two wavelengths. In addition, because the scattered light intensity from the minute defect is in proportion to the minus fourth power of the wavelength, a scattered light intensity ratio of the wavelength of 213 nm and the wavelength of 355 nm is 7.7:1, when illumination intensities are equal to each other. Therefore, it is desirable to set the division ratio to 2 from 10/7.7=1.3 to perform setting such that scattered light outputs from a minute defect become equal to each other. In addition, a detection sensitivity ratio between two wavelengths in the detection optical system 4a or 4b is determined by a transmittance ratio between two wavelengths in an optical element such as a lens or a filter constituting the detection optical system and a detection sensitivity ratio between two wavelengths in the optical detector 405a or 405b. When a sensitivity ratio of the detection optical systems of the wavelength of 213 nm and the wavelength of 355 nm is 1:2, it is desirable to set the division ratio to 4 from 10/7.7×2=2.6 to equalize outputs of the optical detector 405a. The division ratio is set as described above, so that a large difference between wavelengths in the illumination light intensity, the defect scattered light intensity, or the detection signal intensity can be suppressed without lowering use efficiency of the seed light and a dynamic range of the detector can be effectively used.

Figure 4:
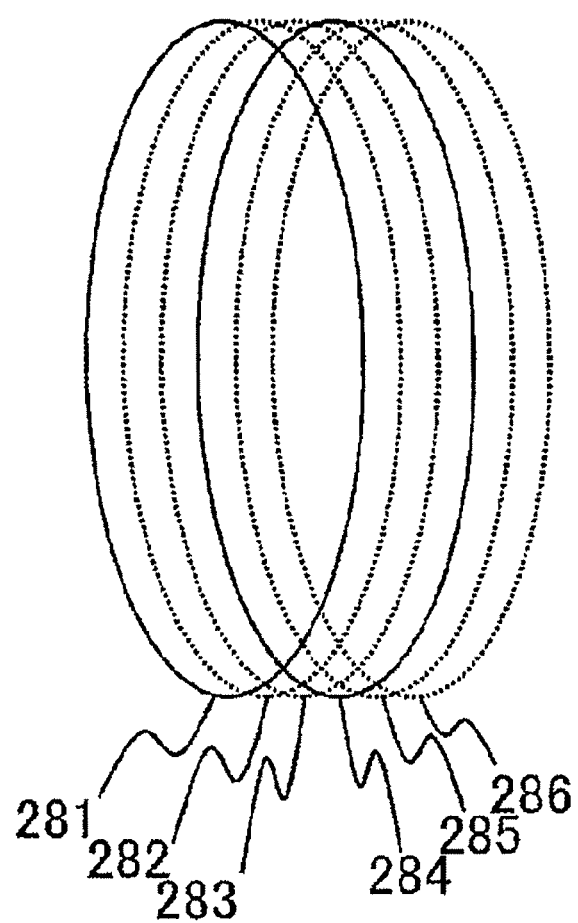
FIG. 4 is a diagram illustrating an example of a relation of a movement speed of an illumination spot and a pulse frequency according to this embodiment.

FIG. 4 illustrates an example of a relation of a movement speed of an illumination spot and a pulse frequency according to this embodiment. An entire surface of the sample S is scanned with an illumination spot on the surface of the sample S by rotation of the sample stage 10 and translation scanning. The illumination spot is elliptical and moves on the sample S in a short diameter direction of the illumination spot. FIG. 4 illustrates an example of the case in which the division ratio of the division signal generator 201 is set to 3 and the pulse number ratio of the wavelengths of 213 nm and 355 nm is 2:1. FIG. 4 illustrates an illumination spot position for each illumination pulse, in a certain time range during scanning of the illumination spot on the sample S. Illumination spot positions 281 and 284 correspond to the pulse of the wavelength of 355 nm and illumination spot positions 282, 283, 285, and 286 correspond to the pulse of the wavelength of 213 nm. In the case of the wavelength of 355 nm, a pulse interval is long. However, illumination spot regions of continuous pulses overlap each other, so that the entire surface of the sample S can be securely inspected. In order to satisfy the above conditions, a scanning speed of the sample stage 10 and a pulse repetitive frequency of the pulse signal generator 101 are set. For example, the pulse repetitive frequency of the pulse signal generator 101 is set to 36 MHz or more under conditions in which the illumination spot width is 5 μm×10 μm, the scanning speed of the sample stage 10 is 30 m/s, and the division ratio N is 3, so that the overlap width of the illumination spot of the wavelength of 355 nm becomes 2.5 μm or more and the same place on the sample S is illuminated two times or more at each wavelength. In addition, the pulse repetitive frequency of the pulse signal generator 101 is set to 53 MHz or more under the same conditions, so that the overlap width of the illumination spot of the wavelength of 355 nm becomes 3.3 μm or more and the same place on the sample S is illuminated three times or more at each wavelength. As such, the same place is radiated with light of the plurality of pulses for each wavelength, so that a variation of a detection signal or reduction of inspection sensitivity of noise due to an intensity variation between the pulses is alleviated.

Figure 5:
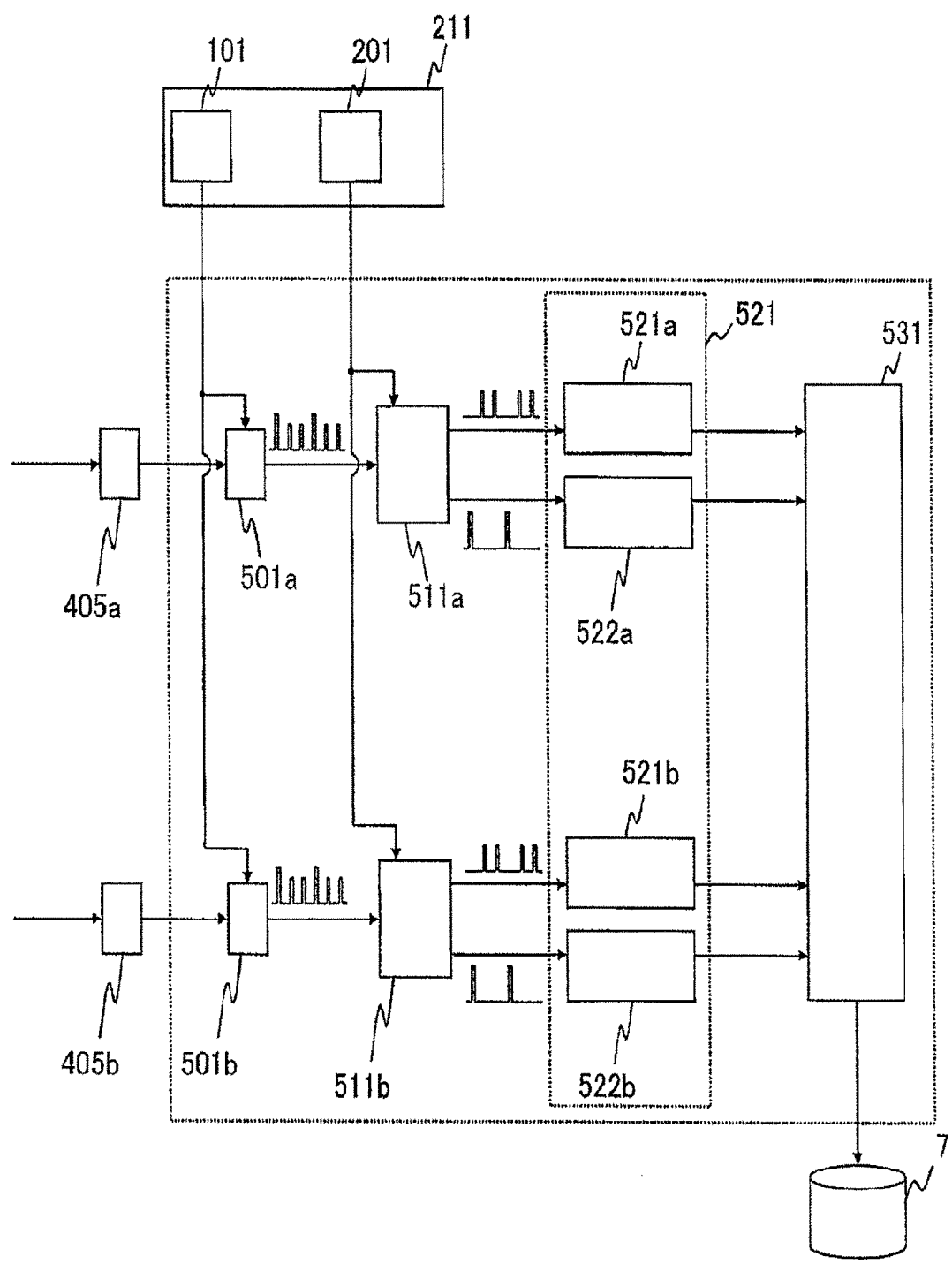
FIG. 5 is a diagram illustrating an example of a configuration of a signal processing unit according to this embodiment.

FIG. 5 illustrates an example of a configuration of the signal processing unit 5 according to this embodiment. The signal processing unit 5 has A/D converters 501a and 501b, distributors 511a and 511b, defect determiners 521a, 521b, 522a, and 522b, and a defect merging unit 531.

A scattered light detection signal detected by the optical detector 405a is converted into a digital signal by the A/D converter 501a. The A/D converter 501a outputs an output signal from the optical detector at only an output time of illumination pulse light and a time (an alleviation time of an output of the optical detector) immediately after the output time and outputs a signal at the other time as 0, on the basis of a signal from the pulse signal generator 101. As a result, only a scattered light signal generated by pulse light is output and a noise component such as a dark current generated by the optical detector is removed. The A/D converter 501a operates at a sampling frequency equal to or higher than the pulse repetitive frequency of the pulse signal generator 101. The distributor 511a receives a signal from the division signal generator 201, separates an output signal of the A/D converter 501a into two signals according to ON/OFF of a pulse signal after the division, and outputs the signals. Thereby, the signal is distributed in synchronization with a polarization state of an output pulse of seed light and a scattered light signal by illumination of light of each of the two wavelengths is separated for each wavelength. The defect determiners 521a and 522a determine the presence or absence of a defect, on the basis of a scattered light signal of each wavelength, and output a result. In the example of FIG. 5, the defect determiners 521a and 522a process the signals of the wavelengths of 213 nm and 355 nm, respectively, and determine the presence or absence of a defect. The same process as the scattered light detection signal detected by the optical detector 405*a* is executed on the scattered light detection signal detected by the optical detector 405*b* and a defect determination result for each wavelength is output to the defect merging unit 531. The defect merging unit 531 compares defect determination results obtained for each wavelength in each of the detection optical systems of the plurality of directions and outputs a sum set thereof as a defect obtained by an inspection.

Figure 6A:
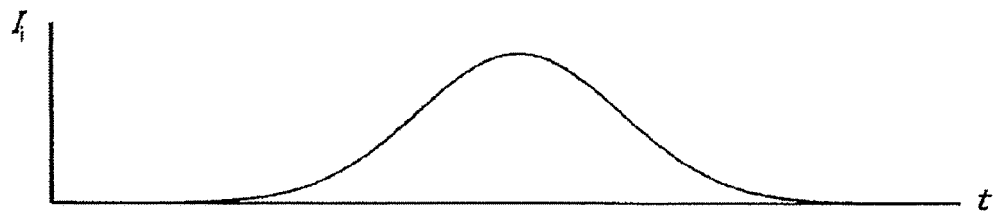
FIGS. 6A to 6D are diagrams illustrating an example of a low-pass filter in a defect determiner according to this embodiment.
Figure 6B:
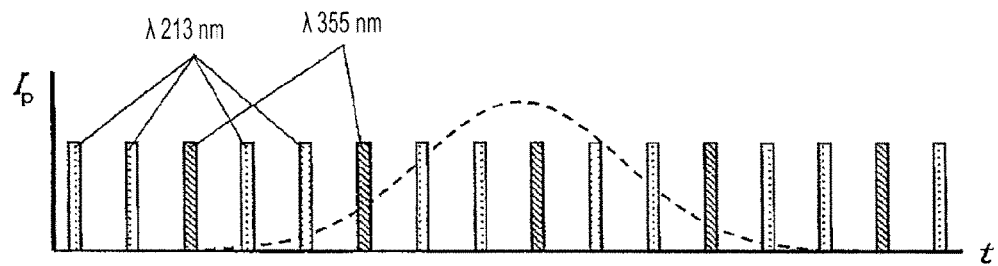
Figure 6C:
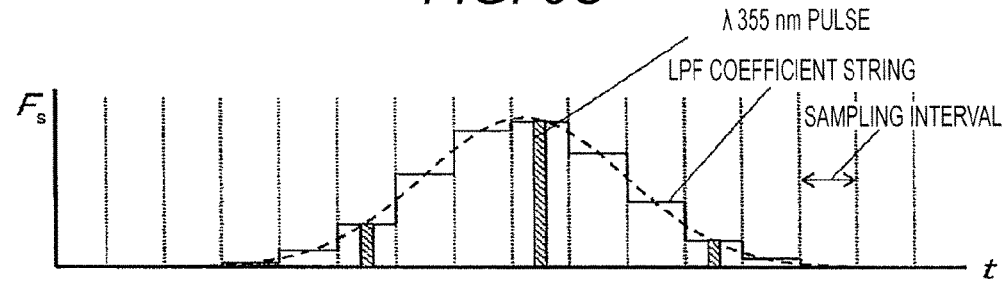
Figure 6D:
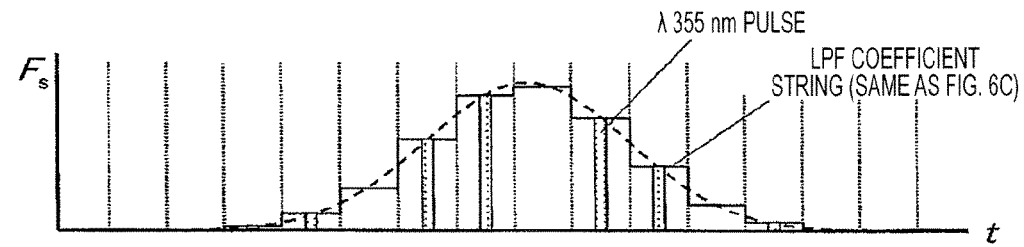

FIGS. 6A to 6D illustrate an example of a low-pass filter (LPF) in the defect determiner according to this embodiment. FIG. 6A illustrates a time change of an illumination power density matched with a certain place of a sample S, when an illumination spot distribution is a Gaussian distribution. FIG. 6B illustrates pulse radiation timing of each wavelength of illumination light. FIG. 6C illustrates pulse radiation timing of the illumination light of the wavelength of 355 nm and a convolution coefficient string of the low-pass filter in the defect determiner. FIG. 6D illustrates pulse radiation timing of the illumination light of the wavelength of 213 nm and a convolution coefficient string of the low-pass filter in the defect determiner. A scattered light signal at each wavelength is intermittently pulsed to correspond to the pulse radiation timing of the illumination light. However, a plurality of pulse signals are obtained for an illumination spot passage time, by setting of the pulse repetitive frequency described using FIG. 4. The low-pass filter of the coefficient string in proportion to the intensity distribution of the illumination spot illustrated in FIGS. 6C and 6D is operated with respect to the intermittent pulse signal of each wavelength output by the distributor, so that continuous scattered light signals corresponding to continuous scanning of the sample by the stage 10 are obtained. In addition, because a frequency band of the low-pass filter is equal to a signal frequency band of a minute defect of a dimension smaller than an illumination spot dimension, a frequency band component other than a signal of the minute defect is reduced and an S/N ratio of a defect signal is improved.

In the defect determiners 521*a*, 522*a*, 521*b*, and 522*b*, in addition to the presence or absence of the defect, defect information such as the defect coordinates, an estimated defect dimension, and an estimated defect type is output for each signal determined as the defect. The determination of the presence or absence of the defect and the calculation of the defect information may be performed by integrating and processing the plurality of input signals input to the plurality of defect determiners 521*a*, 522*a*, 521*b*, and 522*b*. By integrating and processing the signals of the plurality of wavelengths and the plurality of detection directions, the determination of the presence or absence of the defect and the calculation of the defect information can be performed with high precision. Alternatively, the signal intensity or the partial signal waveform profile of each signal determined by the defect determiner that a defect is likely to be present may be output and the defect merging unit 531 may determine the presence or absence of a defect again, calculate the defect information such as the defect coordinates, the estimated defect dimension, and the estimated defect type, and may output the defect information. In this case, because the integration process of the signals of the plurality of wavelengths and the plurality of detection directions is executed on only fragments of the signals determined by the defect determiner that a defect is likely to be present, the determination of the presence or absence of the defect and the calculation of the defect information are performed with high precision and a process load is alleviated.

Second Embodiment

In this embodiment, an example of the case in which two wavelengths of 266 nm and 355 nm are used as a plurality of wavelengths will be described.

Figure 7:
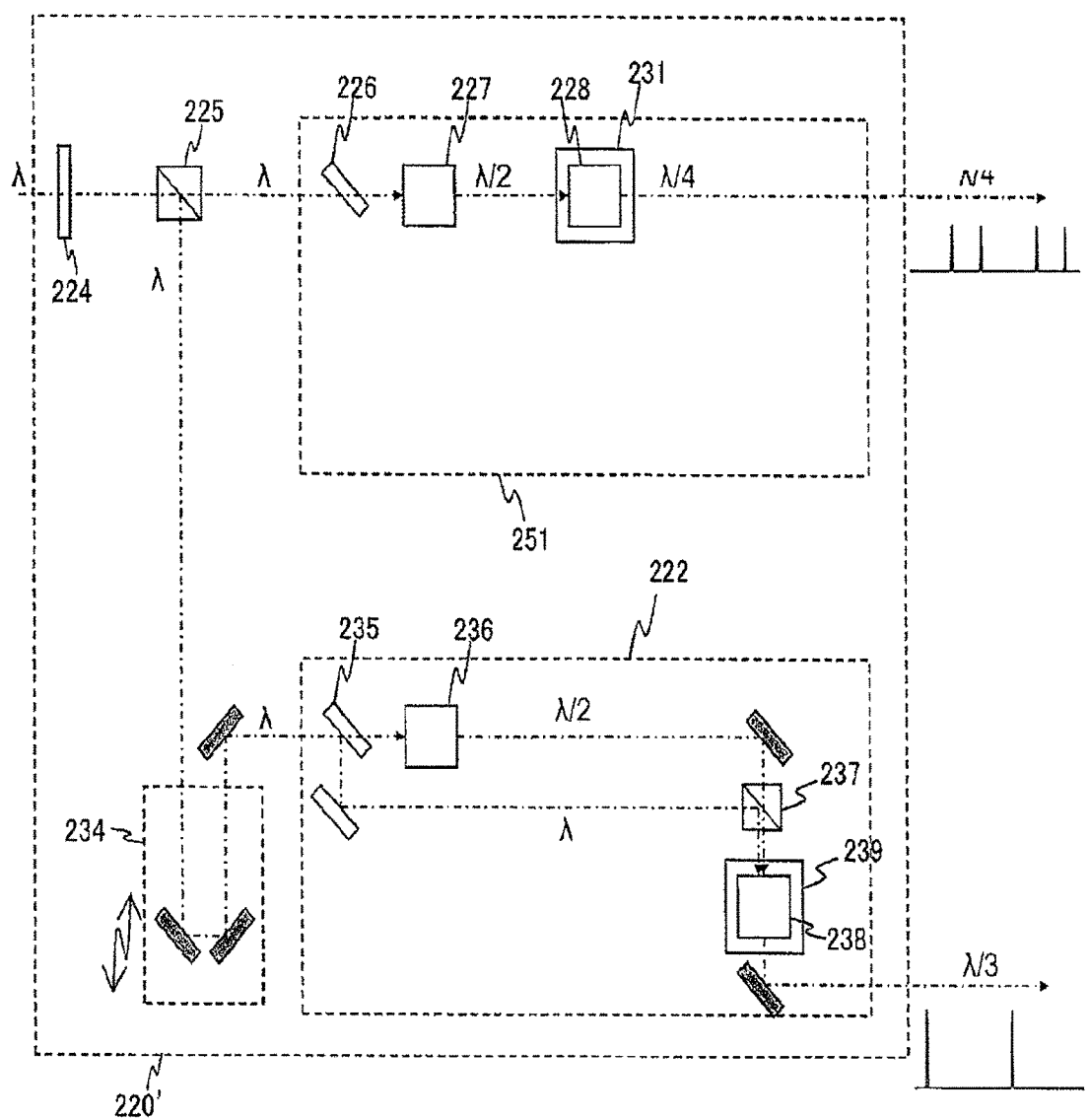
FIG. 7 is a diagram illustrating an example of a configuration of a wavelength converting unit according to a second embodiment.

FIG. 7 illustrates an example of a configuration of a wavelength converting unit 220' according to the second embodiment. In this embodiment, the wavelength converting unit 220 according to the first embodiment is changed to the wavelength converting unit 220'. Because the other configurations have the same functions as the configurations illustrated in FIG. 1 described above and denoted with the same reference numerals, explanation thereof is omitted.

The wavelength converting unit 220' has a wavelength plate 224, a polarization beam splitter 225, a fourth harmonic converting unit 251, a third harmonic converting unit 222, and a pulse delay unit 234. Seed light (a wavelength of 1064 nm) output by a seed light generator 211 is adjusted in polarization state by the wavelength plate 224, is branched by the polarization beam splitter 225, is converted into fourth harmonics (a wavelength 266 nm) by the fourth harmonic converting unit 251, and is converted into third harmonics (a wavelength 355 nm) by the third harmonic converting unit 222. The pulse delay unit 234 compensates for a difference of optical path lengths of the fourth harmonic converting unit 251 and the third harmonic converting unit 222.

One beam separated by the polarization beam splitter 225 is incident on the fourth harmonic converting unit 251. The beam is branched by a beam splitter 226, a wavelength of the beam is converted into a wavelength of 532 nm (second harmonics) by second harmonic generation by a wavelength conversion crystal 227 and is converted into a wavelength of 266 nm (fourth harmonics) by second harmonic generation by a wavelength conversion crystal 228 again, and the beam is output.

After an optical path difference of another beam separated by the polarization beam splitter 225 and other beam is adjusted by the pulse delay unit 234 configured using a folding mirror or a corner cube, the beam is incident on the third harmonic converting unit 222. The beam is branched by a beam splitter 235, a wavelength of the beam is converted into a wavelength of 532 nm (second harmonics) by second harmonic generation by a wavelength conversion crystal 236, the beam is synthesized with a beam branched into a different optical path by the beam splitter 235 by a dichroic mirror 237, the wavelength of the beam is converted into a wavelength of 355 nm (third harmonics) by sum frequency generation by a wavelength conversion crystal 238, and the beam is output.

As compared with the wavelength of 213 nm (fifth harmonics) used in the first embodiment, because the wavelength of 266 nm (fourth harmonics) used in the second embodiment is relatively long, a restriction of an optical element material constituting an optical system is small and damage applied to an optical element is small. Therefore, costs and running costs of an illumination optical system and a detection optical system can be decreased.

Third Embodiment

In this embodiment, an example of the case in which illumination light of different wavelengths are output from the same illumination optical system will be described.

Figure 8:
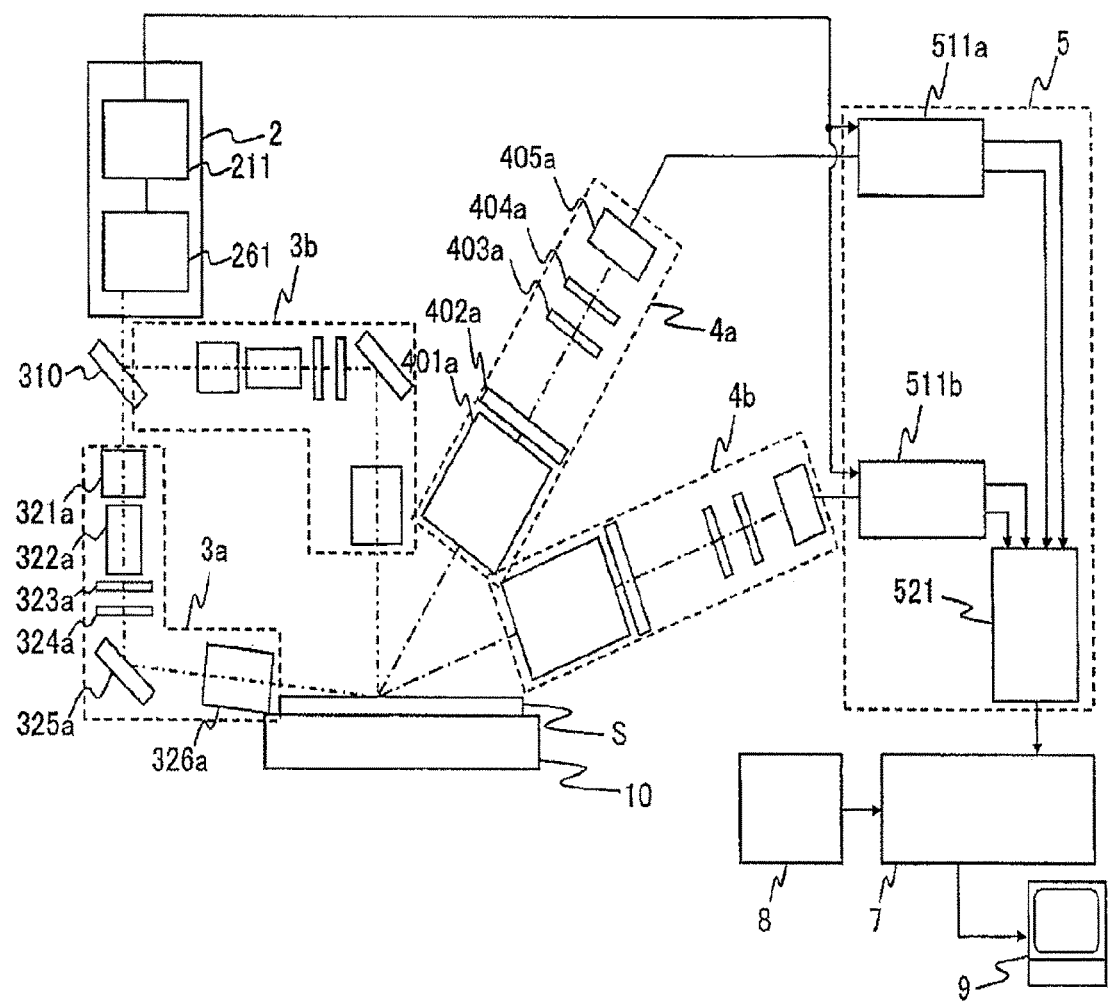
FIG. 8 is a diagram illustrating an example of a configuration of a defect inspection apparatus according to a third embodiment.

FIG. 8 illustrates an example of a configuration of a defect inspection apparatus according to a third embodiment. In this embodiment, the wavelength converting unit 220 according to the first embodiment is changed to a wavelength converting unit 261. By a configuration of the wavelength converting unit 261 to be described below, laser beams of two wavelengths are emitted from a light source 2 at the same optical axis. By moving in/out a mirror 310, an optical path of the beam emitted from the light source 2 is changed and the beam is guided to an illumination optical system 3a or 3b. The illumination optical system 3a has an attenuator 321a, a beam expander 322a, a λ/2 plate 323a, a λ/4 plate 324a, a mirror 325a, and an illumination condensing system 326a. The attenuator 321a, the beam expander 322a, the λ/2 plate 323a, the λ/4 plate 324a, the mirror 325a, and the illumination condensing system 326a correspond to the two wavelengths of the light emitted from the light source 2 or suppress wavelength dependency over a wide wavelength band including the two wavelengths. A refraction optical system including lenses of a plurality of materials, a catadioptric system including a curved reflection surface in which there is not the chromatic aberration, or a reflection optical system is used as the illumination condensing system 326a to suppress the wavelength dependency and the chromatic aberration. The illumination optical system 3b has the same configuration as the illumination optical system 3a. Because the other configurations have the same functions as the configurations illustrated in FIG. 1 described above and denoted with the same reference numerals, explanation thereof is omitted.

Figure 9:
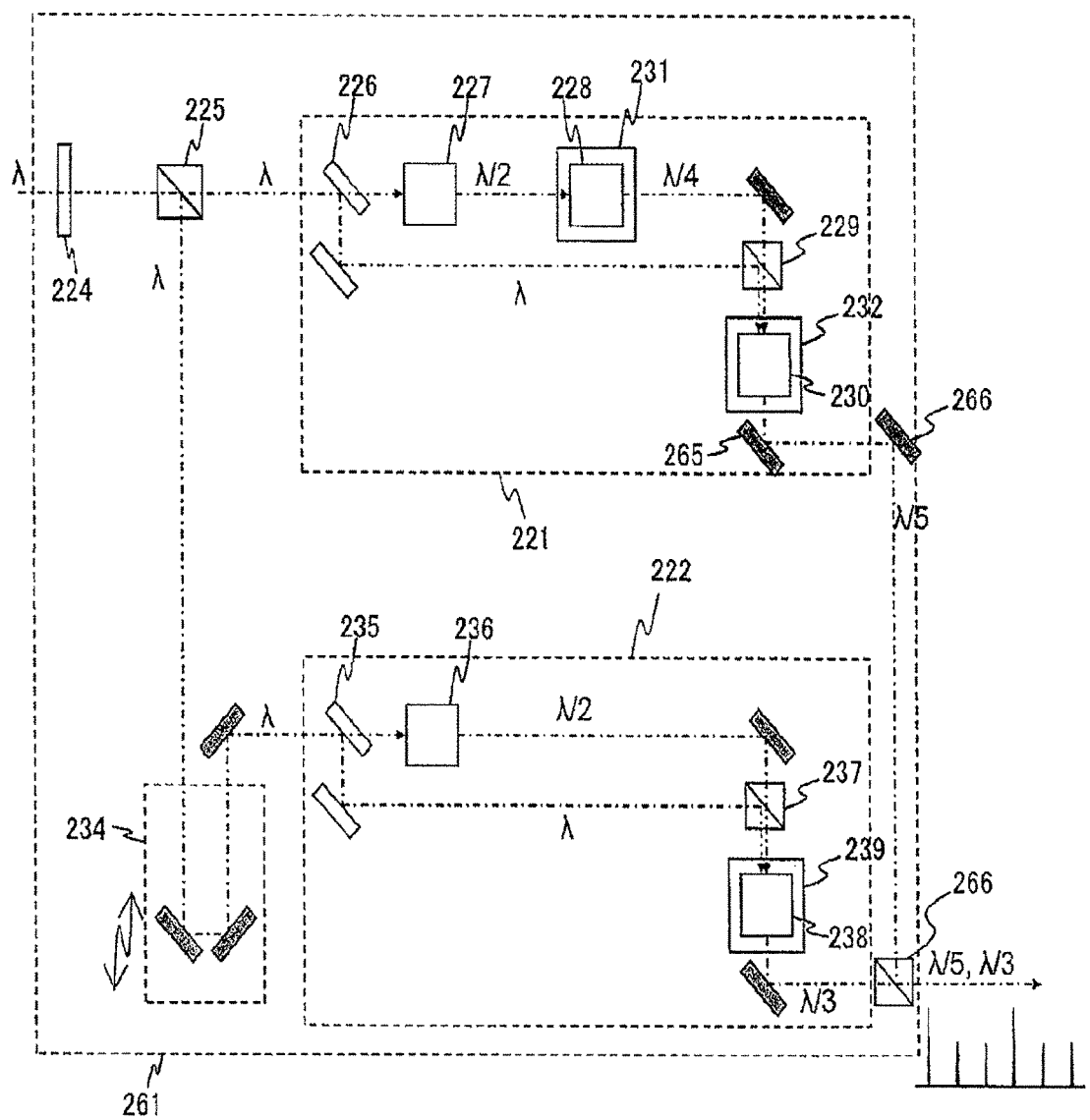
FIG. 9 is a diagram illustrating an example of a configuration of a wavelength converting unit according to the third embodiment.

FIG. 9 illustrates an example of a configuration of the wavelength converting unit according to the third embodiment. A difference with the wavelength converting unit 220 according to the first embodiment described using FIG. 3 will be described. A beam converted into fifth harmonics (a wavelength of 213 nm) by a fifth harmonic converting unit 221 is adjusted in beam optical axis position and angle by mirrors 265 and 266, is overlapped to third harmonics (a wavelength of 355 nm) output from a third harmonic converting unit 222 at the same optical axis in a dichroic mirror 267, and is output from a wavelength converting unit 261. In this embodiment, two wavelength oblique illumination or two wavelength vertical illumination is enabled. The two wavelength oblique illumination is effective for detecting minute foreign materials or convex defects of a plurality of materials. The two wavelength vertical illumination is effective for detecting flat large defects of a plurality of materials.

Fourth Embodiment

In this embodiment, an example of the case in which optical paths of two wavelengths are branched and detection is performed in a detection optical system will be described.

Figure 10:
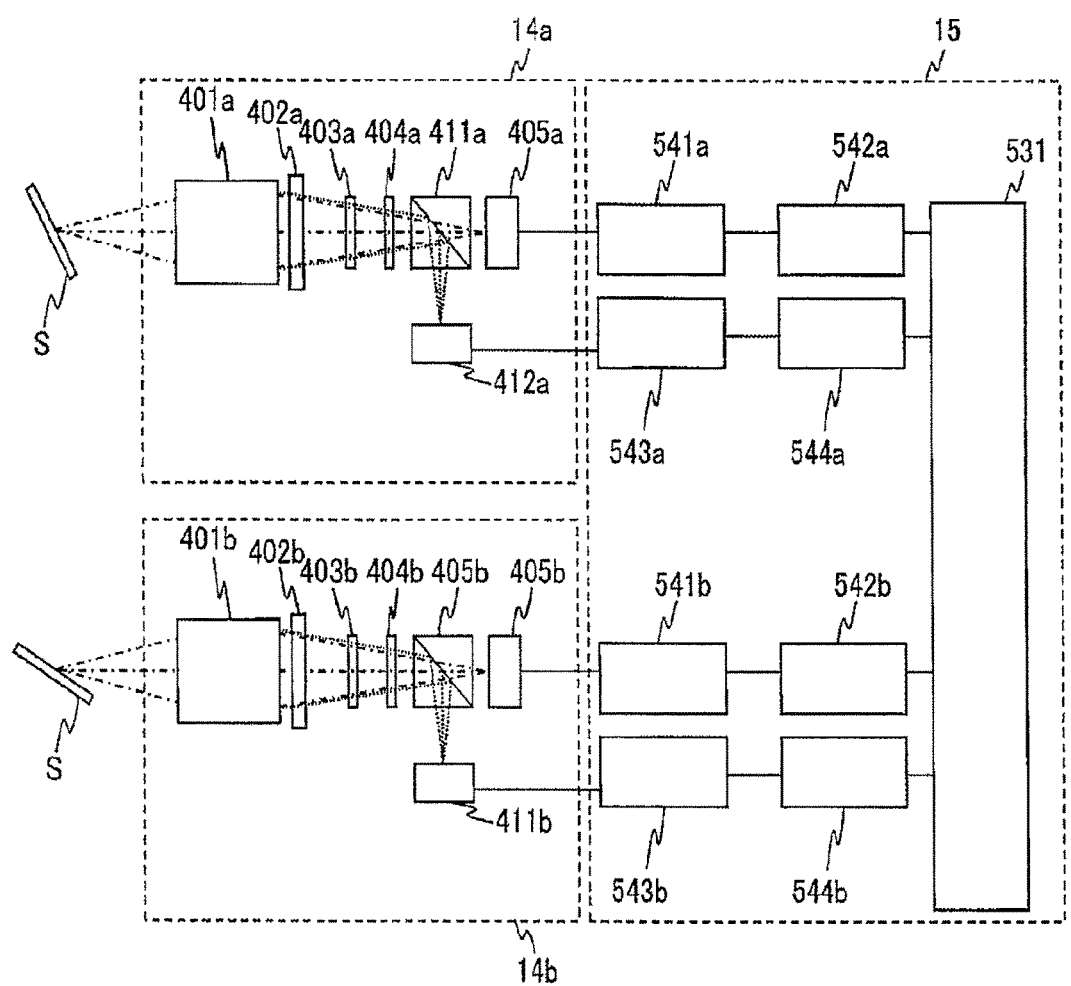
FIG. 10 is a diagram illustrating an example of configurations of a detection optical system and a signal processing system according to a fourth embodiment.

In this embodiment, the detection optical systems 4a and 4b and the signal processing unit 5 according to the first embodiment are changed to detection optical systems 14a and 14b and a signal processing system 15 illustrated in FIG. 10. Because the other configurations have the same functions as the configurations illustrated in FIG. 1 described above and denoted with the same reference numerals, explanation thereof is omitted.

FIG. 10 illustrates an example of configurations of the detection optical system and the signal processing system according to the fourth embodiment. The detection optical system 14b has the same configuration as the detection optical system 14a. The detection optical system 14a according to this embodiment includes a detection condensing system 401a, a space filter 402a, a λ/4 plate 403a, a polarization plate 404a, a dichroic mirror 411a, and optical detectors 405a and 412a. The functions of the detection condensing system 401a, the space filter 402a, the λ/4 plate 403a, and the polarization plate 404a are common to the functions in the first embodiment. Light that is emitted from an illumination spot and is condensed by the detection condensing system 401a is branched by the dichroic mirror 411a for each wavelength, the light of each optical path is detected by each of the optical detectors 405a and 412a, and a detection signal for each wavelength is output. The optical detectors 405a and 412a are arranged in the vicinity of condensing positions of the light of the individual wavelengths.

In the signal processing system 15, the detection signals for the individual wavelengths obtained by the detection optical systems 14a and 14b are converted into digital signals by A/D converters 541a, 543a, 541b, and 543b, the presence or absence of a defect is determined by defect determiners 542a, 544a, 542b, and 544b, results are merged by a defect merging unit 531, and a merged result is output.

In this embodiment, even when condensing positions are different according to wavelengths for the on-axis chromatic aberration of the detection condensing system 401a, detection at the condensing position is enabled by position adjustment of each of the optical detectors 405a and 412a. Therefore, the detection condensing system 401a can be realized at a low cost. Because the on-axis chromatic aberration is allowed, the detection condensing system 401a of a high NA or a wide field can be realized. In addition, because it is not necessary to separate a repetitive pulse of illumination light and perform detection, a detector of a high-speed response does not need to be used and the optical detectors 405a and 412a can be realized at a low cost.

The present invention is not limited to the embodiments described above and various modifications are included in the present invention. For example, the above embodiments are described in detail to facilitate the description of the present invention and are not limited to embodiments in which all of the described configurations are included. In addition, a part of the configurations of the certain embodiment can be replaced by the configurations of another embodiment or the configurations of another embodiment can be added to the configurations of the certain embodiment. In addition, for a part of the configurations of the individual embodiments, other configurations can be added, deleted, and replaced.

In addition, only control lines or information lines that are necessary for explanation are illustrated and do not mean all control lines or information lines necessary for a product. In actuality, almost all configurations may be connected to each other.

What is claimed is:

1. A defect inspection apparatus comprising:
   a seed light generator including a pulse signal generator that generates a pulse signal and a polarization modulator that outputs pulse light in either of two polarization states orthogonal to each other and in synchronization with the pulse signal;
   a wavelength converter that branches the pulse light using polarization and wavelength-converts the branched pulse light into beams of two different wavelengths, respectively;
   an optical illuminator that illuminates a surface of an inspected target material with the beams of two different wavelengths, each of the beams being applied at different times corresponding to their respective orthogonal polarization states;

an optical detector that detects light generated by the beams of two different wavelengths illuminated by the illumination optical system; and a signal processor that distributes a signal based on the light detected by the optical detector and based on the pulse signal, and a defect detector that processes a signal based on the light distributed by the signal processor and determines a defect, wherein the wavelength converter includes a pair of harmonic converters such that an intensity ratio between the pair of converters is (N−1):1 and a ratio of pulse numbers per unit time in a beam incident to one of the pair of harmonic converters and a beam incident to another of the pair of harmonic converts is (N−1):1, where N=4 and a first intensity of a first output of the optical detector due to a first wavelength of light scattered by a minute defect is approximately equal to a second intensity of a second output of the optical detector due to a second wavelength of light scattered by the minute defect.

2. The defect inspection apparatus according to claim 1, wherein:

the wavelength converter includes any one of a combination of a fifth harmonic converter and a third harmonic converter, and a combination of a fourth harmonic converter and the third harmonic converter.

3. The defect inspection apparatus according to claim 1, wherein:

the signal processor merges a defect determination result determined by the defect detector.

4. The defect inspection apparatus according to claim 1, wherein:

the wavelength converter overlaps the beams of two different wavelengths that are wavelength-converted on the same optical axis and outputs the beams.

5. A defect inspection method comprising:

generating seed light including generating a pulse signal and performing polarization modulation for outputting pulse light in either of two polarization states orthogonal to each other and in synchronization with the pulse signal;

converting wavelength including branching the pulse light using polarization and wavelength-converting the branched pulse light into beams of two different wavelengths, respectively;

performing an illumination optical process of illuminating a surface of an inspected target material with the beams of two different wavelengths, each of the beams being applied at different times corresponding to their respective orthogonal polarization states;

performing a detection optical process including detecting light generated by the beams of two different wavelengths illuminated by the illumination optical process; and performing a signal processing process including distributing a signal based on the light detected by the detection of the detection optical process and based on the pulse signal, and processing a signal based on the light distributed by the distribution, and determining a defect, wherein the wavelength converter includes a pair of harmonic converters such that an intensity ratio between the pair of converters is (N−1):1 and a ratio of pulse numbers per unit time in a beam incident to one of the pair of harmonic converters and a beam incident to another of the pair of harmonic converts is (N−1):1, where N=4 and a first intensity of a first output of the optical detector due to a first wavelength of light scattered by a minute defect is approximately equal to a second intensity of a second output of the optical detector due to a second wavelength of light scattered by the minute defect.

6. The defect inspection method according to claim 5, wherein:

in the conversion of the wavelength conversion, any one of a combination of fifth harmonic conversion and third harmonic conversion and a combination of fourth harmonic conversion and the third harmonic conversion is performed.

7. The defect inspection method according to claim 5, wherein:

the signal processing process includes merging a defect determination result based on the signal based on the light distributed by the distribution, which has been determined by the defect determination.

8. The defect inspection method according to claim 5, wherein:

the wavelength conversion overlaps the beams of the two different wavelengths wavelength-converted by the conversion on the same optical axis and outputs the beams.

* * * * *